United States Patent [19]

Komatsu

[11] Patent Number: 4,862,746
[45] Date of Patent: Sep. 5, 1989

[54] VIBRATION TESTER FOR SCREWS

[76] Inventor: Minoru Komatsu, 1-544, Ikebukuro, Toshima-ku, Tokyo, Japan

[21] Appl. No.: 26,212

[22] Filed: Mar. 16, 1987

[51] Int. Cl.$^4$ ............................................. G01N 3/36
[52] U.S. Cl. ......................................... 73/572; 73/12; 73/761; 73/663
[58] Field of Search ................ 73/570, 572, 581, 662, 73/663, 761, 865.3, 12

[56] References Cited

FOREIGN PATENT DOCUMENTS 000487  1/1977  Japan ..................................... 73/572

Primary Examiner—John Chapman
Attorney, Agent, or Firm—Edmund M. Jaskiewicz

[57] ABSTRACT

A vibration tester for measuring the looseness of thread connections is disclosed which comprises a support frame, a specimen holding section mounted in the support frame and a pair of pneumatic hammers mounted at both ends of the specimen holding section. The specimen holding section consists of a largely cylindrical shaped hollow holder, a strain gauge provided and attached to the gauge carrier for measuring the looseness of specimens, a vibrating plate mounted on the hollow holder in contact with the pneumatic hammers in such a manner as to be subjected to blows from the pneumatic hammers, and a guide mechanism adapted to guide the direction of pneumatic hammer blows. With this arrangement, the pneumatic hammers are activated to deliver impacts to the vibrating plates, with the bolt making up the specimen set on the tester by being inserted through the gauge carrier, hollow holder and vibratory plate, with the nut tightened to the protruding end of the bolt. The looseness of the specimen occurring as a result of such blows is read on the strain gauge. The tester of this invention is capable of testing all types of thread connections, whatever size they may be of, with increased reliability.

3 Claims, 5 Drawing Sheets

4,862,746

VIBRATION TESTER FOR SCREWS

BACKGROUND OF THE INVENTION

1. Field of the Invention

This invention relates to a vibration tester for screws and bolts in which the specimen is checked for looseness by subjecting it to impact or vibration.

2. Description of the Prior Art

In the prior art, various devices for testing the looseness of screws and bolts have been developed. A representative such tester is illustrated in FIGS. 1 and 2, which comprises a shaft 62, which may be mounted in a box 61, which is vertically vibrationally disposed. Onto the shaft 62 is fixedly mounted a jig 63 having a plurality of slits 64 formed therein. To test a specimen for looseness, it is inserted into the slits 64, as depicted in FIG. 2, and exposed to violent vibration by oscillating the shaft 2. The specimen has a sleeve 66. A bolt 67 is passed through the sleeve 66 and fixed in position with a nut 68 that is tightened against the bolt's head 67a. With this arrangement, the looseness of the nut 68 is measured by a strain gauge S fitted onto the sleeve 66.

These conventional vibration testers have been found universally unacceptable for application with all available sorts of nuts since they lack the ability to cause looseness in high-tension locking nuts.

It is this drawback of the prior art testers that gave rise to the present invention. It is therefore a primary object of the present invention to provide a vibration tester capable of testing a wide range of bolts and screws for looseness by subjecting them to strong impact.

SUMMARY OF THE INVENTION

The above and other objectives, features and advantages of this invention are achieved by a device which comprises a support frame for holding specimens or nuts and bolts in pairs to be tested, and a pneumatic hammer which delivers impacts to the specimen. The support frame, in turn, consists of a cylindrical shaped support member, a 15 gauge carrier detachably mounted inside the hollow of the support member, a strain gauge attached to the gauge carrier for measuring the looseness of the specimen, a vibrating plate mounted on the support member in such a manner as to hold its surface when subjected to the blows from the 20 pneumatic hammer, and a guide mechanism which guides the direction of blows from the hammer. In operation, the bolt is inserted through the gauge carrier, the support member and the vibratory plate and tightened together in fixed position by the nut. Then, the pneumatic hammer is actuated to deliver blows to the vibrating plate causing the specimen to become loose. The gauge is read to determine the resultant looseness in the nut.

DETAILED DESCRIPTION OF PREFERRED EMBODIMENTS

Preferred embodiments of the present invention are described in great detail in conjunction with the accompanying drawings.

Figure 1:
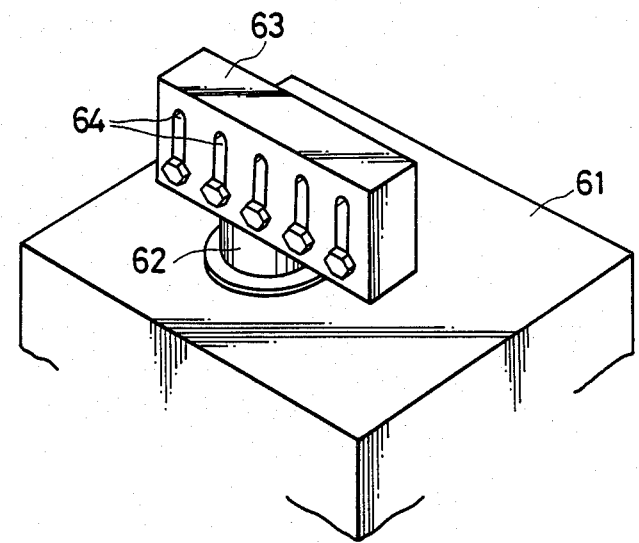
FIG. 1 is a perspective view of a conventional device for testing looseness.
Figure 2:
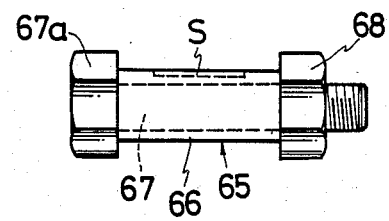
FIG. 2 is a front view of a specimen set on the device shown in FIG. 1.
Figure 3:
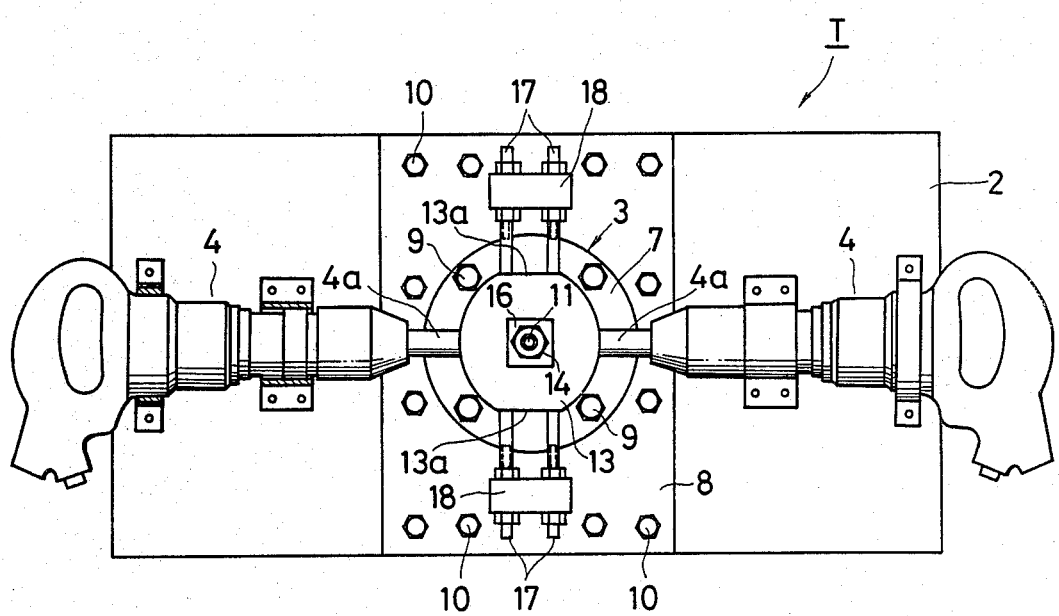
FIG. 3 is a vibration tester for screws constructed in accordance with the present invention.
Figure 4:
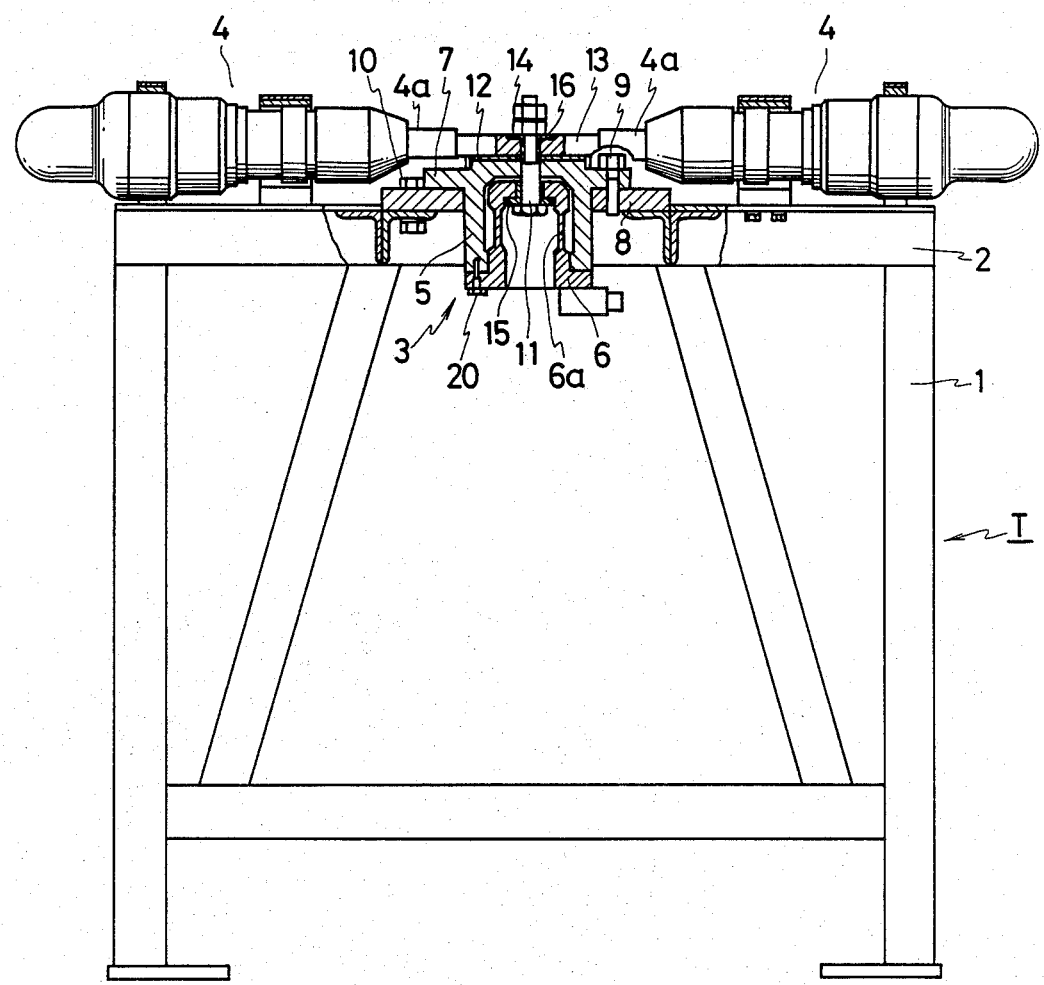
FIG. 4 is a side view of the tester in FIG. 3.

Referring first to FIGS. 3 and 4, a vibration tester T for screws in accordance with a preferred embodiment of the present invention consists of a support frame 1 and a support plate 2 mounted in the support frame. In the middle of the support plate 2 is mounted a specimen holding section 3 that is adapted to hold a set of a bolt and nut to be tested for looseness. A pair of pneumatic hammers 4 are mounted in fixed positions in the support plate 2 on both sides of the holding section 3. The holding section 3 comprises a cylindrically shaped hollow holder 5 adapted to carry therein a gauge carrier 6 to which a strain gage, not shown, is attached. The holding section 3 has in an upper end of its side a flange portion 7. To the flange portion 7 is fixedly attached a mounting plate 8 through bolts 9. The mounting plate 8, in turn, secured to the support plate 2 through bolts 10 and is immobile.

The gauge carrier 6 is built with a largely bell shape so that it can be housed inside the holder 5. Also, the carrier 6 has a thin-walled portion 6a in its side to receive therein the strain gauge, not shown. An opening is formed in the upper side of the gauge carrier 6. The holder is also provided in its top portion with an opening in alignment with the opening of the gauge carrier 6. A bolt 11 is inserted in an upward direction into both openings to project through a central opening that is formed in vibrating plate 13 mounted on top of the holder 5 through a sintered plate washer 12. A nut 14 is tightened onto the projected end of the inserted bolt 11. A bushing 15 is fitted in the top opening of the gauge carrier 6.

A square washer 16 is provided between the nut 14 and the central opening of the vibrating plate 13. The vibrating plate 13 is cut at its circumference to form a pair of guide surfaces 13a. Guide rods 17 are provided in such manner as to make contact with the guide surfaces 13a, thereby causing the vibrating plate 13 to vibrate in a specific direction as it is hit by the pneumatic hammer 4. Each pneumatic hammer has its vibrating rod contacted with an arcuate portion in the vibrating plate 13. Each of the guide rods 17 is adjustably mounted in a fixed member 18 secured and immobile in the mounting plate 8 such that the guide rods 17 can adjust their protruded length.

Now, the operation of the present invention will be described to provide a better understanding of its mechanism. To test a bolt 11, a gauge carrier 6 sized to meet the diameter of the bolt is prepared. First, the gauge carrier 6 is inserted into the hollow inside of the holder 5 and secured through its lower portion to the holder 5. The bolt 11 is then pushed through the openings until its tip comes above the vibratory plate 13. A nut 14 is tightened onto the projected end of the bolt 11. The pneumatic hammers 4 are then activated delivering impacts to the vibratory plate 13 from opposite directions. If hammering causes the nut 14 to loosen, tension exerted on the gauge carrier 6 decreases. The resultant degree of looseness is read on the strain gauge, not shown, carried in the gauge carrier 6.

The tester according to the present invention can accommodate all kinds of nut and bolt sets whatever size they may be, simply by selecting a correspondingly large hammer impact.

Figure 5:
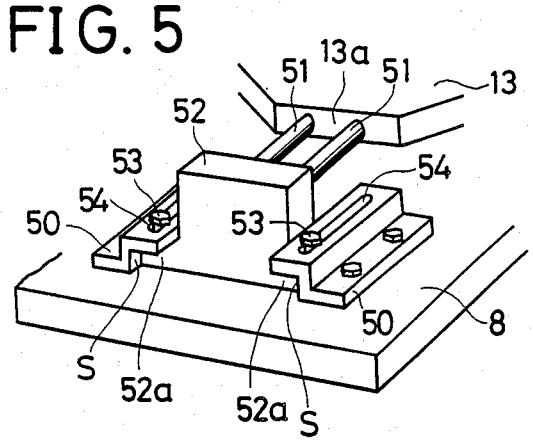
FIG. 5 is a perspective view of the guide mechanism for the vibrating plate in accordance with a second embodiment of this invention.

Referring to FIG. 5, the vibrating plate 13 may have a guide mechanism as shown, instead of the above, in which guide frames 50 are provided and placed side-by-side in the mounting plate 8. A moving member 52 carries in a downward direction the projecting portions 52a each having a guide rod fixed thereto, with the projecting portions being slidably disposed in gaps S defined in the guide frames 50. Also, the projecting portions 52a are each provided with bolts 53 that are inserted through slits 54 formed in the upper surfaces of the guide frames 50. The bolts 53 may be tightened to adjust the position of the guide rods 51, after the moving member 52 is adjusted into the appropriate position.

With respect to the above embodiment described in association with FIGS. 3 and 4, the tester T is designed such that the specimen holding section 3 is held in a horizontal position. Because of this, the gauge carrier 6 has to be inserted into the holder 5 from below. In addition, the bolt 11 has to be inserted into the cavity of the gauge carrier.

These preparatory operations require somewhat cumbersome and complicated work.

Figure 6:
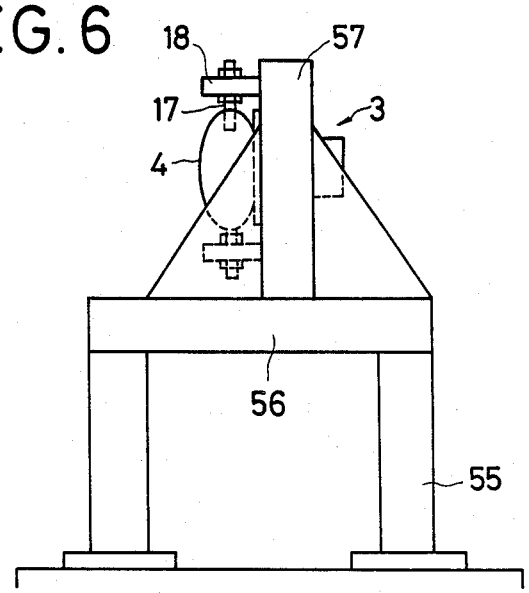
FIG. 6 is a side view of the vibration tester according to a third embodiment of the present invention.

To eliminate the above problem, a support frame 55 may be provided with a horizontal support frame 56 and a vertical support plate 57 be mounted on the horizontal support frame 56, as illustrated in FIG. 6. The pneumatic hammers 4, the specimen holding section 3 and the guide rods 17 are mounted in vertical positions on the vertical support frame 57, along with the fixing member 18. This arrangement is intended to enable the gauge carrier 8 and bolt 11 to be changed with increased ease.

Figure 7:
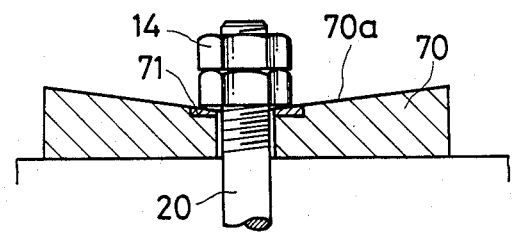
FIG. 7 is a vertical cross-sectional view of the vibrating plate.
Figure 8:
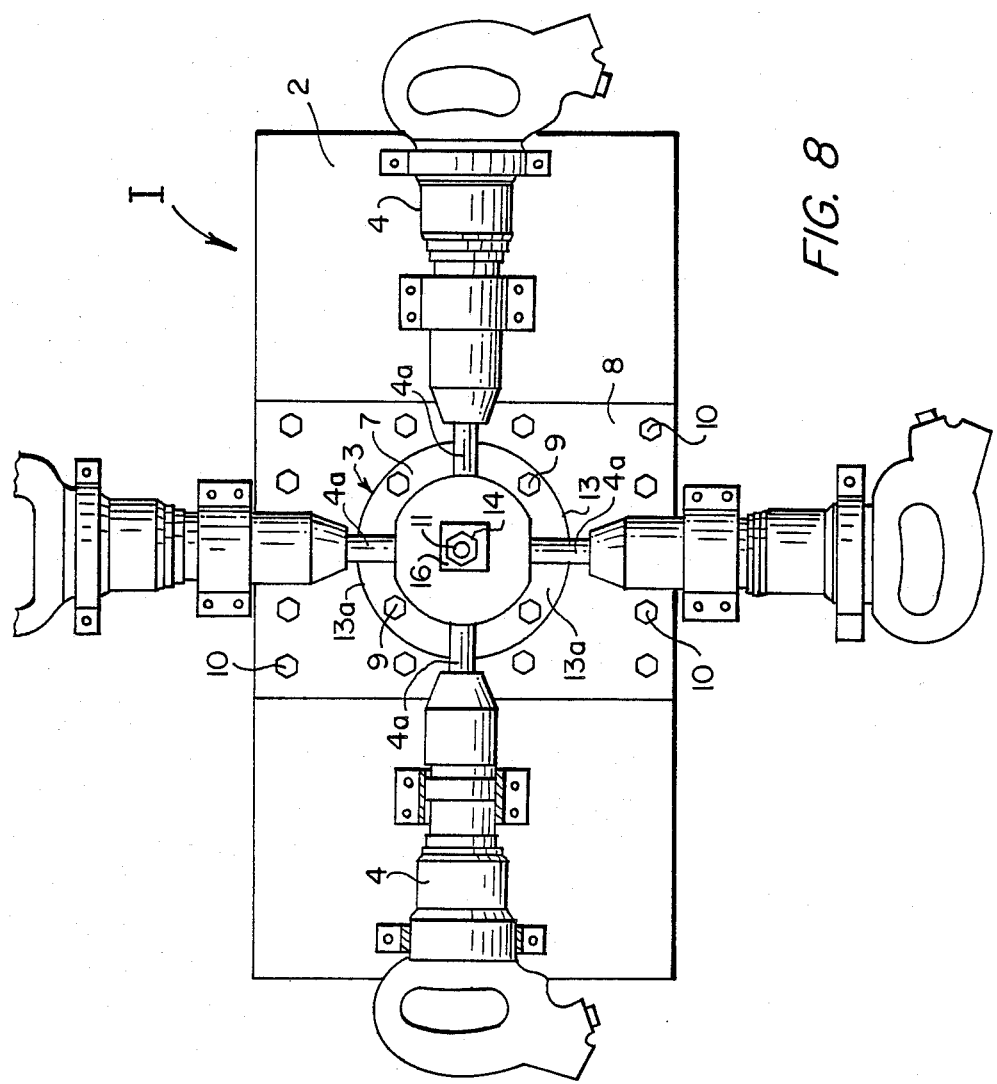
FIG. 8 is a view similar to FIG. 3 but showing a modification of the present invention wherein four pneumatic hammers are used.

With pneumatic hammers having weak impact, looseness cannot be induced in some kinds of nuts tightened on bolts. In such a case, the vibrating rod 4a may be adjusted to increase oscillations enough to obtain the required impact. Alternatively, the vibrating plate 13 may be provided with four pneumatic hammers installed so that they hit the plate from four directions, as shown in FIG. 8. However, it is important to note that, if the vibrating rod 4a is adjusted to an excessively large oscillation, the bolt 11 will be exposed to greater impact than the nut 14, with the result that the bolt 11 breaks. In order to prevent bolt-breakage during the test, the surface 70a of the vibrating plate 70 may be tilted slightly toward the center, as shown in FIG. 7, and a washer 71 that is inclined to the same angle as the vibrating plate 70 may be provided. With this arrangement, when the vibrating plate 70 is oscillated laterally, the nut 14 is caused to take vertical vibration due to the inclined surface of the washer 71 and the vibrating plate 70 so that the tightness between the nut and bolt can be measured with increased reliability. The washer 71 may be spared. Furthermore, the vibrating plate 70 may be formed into an inclined surface only where it is contacted with the nut 14.

It will be easily appreciated that the tester according to the present invention is capable to producing large test impacts so that it can test all existing nuts and bolts and, in addition, can be constructed with a very simple structure.

I claim:

1. A vibration tester for threaded connections comprising a support frame, a specimen holding section mounted in the said support frame, the said specimen holding section being adapted to hold a specimen composed of a nut tightened onto a bolt to be tested, and a pair of pneumatic hammers mounted at opposite ends of said specimen holding section, the said specimen holding section consisting of a hollow holder of a largely cylindrical shape, a gauge carrier detachably mounted in the hollow of the said hollow holder, a strain gauge provided and attached to the said gauge carrier for measuring looseness of said specimen, a vibrating plate mounted on the said holder in contact with the said pneumatic hammers in such a manner as to be subjected to the blows from the said pneumatic hammers, and a guide mechanism adapted to guide the direction of pneumatic hammer blows against the said vibratory plate, wherein the said pneumatic hammers are actuated to deliver impacts to the said vibrating plate, with the said bolt being set on the said tester by penetrating through the said gauge carrier, holder and vibrating plate, with the said nut tightened to the protruding end of the said bolt the looseness of the said specimen as a result of the said impacts being read on the said strain gauge.

2. A vibration tester as set forth in claim 1, wherein the surface of said vibratory plate is slightly inclined toward the center.

3. A vibration tester for thread connections comprising a support frame, a specimen holding section mounted in said support frame, said specimen holding section being adapted to hold a specimen composed of a nut tightened onto a bolt to be tested, and four pneumatic hammers mounted around said specimen holding section, said specimen holding section consisting of a hollow holder of a largely cylindrical shape, a gauge carrier detachably mounted in the hollow of said hollow holder, a strain gauge provided and attached to said gauge carrier for measuring looseness of said specimen, a vibrating plate mounted on said holder in contact with said pneumatic hammers in such a manner as to be subjected to impacts from said pneumatic hammers from four directions, wherein the said pneumatic hammers are actuated to deliver impacts to said vibrating plate, with said bolt being set on the said tester by penetrating through said gauge carrier, holder and vibrating plate, with said bolt tightened to the protruding end of said bolt, the looseness of said specimen as a result of said impacts being read on said strain gauge.

* * * * *